United States Patent

Carls et al.

[11] Patent Number: 5,575,793
[45] Date of Patent: Nov. 19, 1996

[54] PATELLA CLAMP APPARATUS

[75] Inventors: Thomas A. Carls; Khosrow Naraghian; Chris E. Johnson, all of Memphis, Tenn.

[73] Assignee: Smith & Nephew Richards Inc., Memphis, Tenn.

[21] Appl. No.: 389,098

[22] Filed: Feb. 15, 1995

[51] Int. Cl.$^6$ .................................................. A61B 17/56
[52] U.S. Cl. .................................. 606/80; 606/88; 606/96
[58] Field of Search .............................. 606/88, 87, 86, 606/89, 82, 80, 79, 96, 97, 102, 205, 206, 207

[56] References Cited

U.S. PATENT DOCUMENTS

| | | |
|---|---|---|
| 4,565,192 | 1/1986 | Shapiro . |
| 4,633,862 | 1/1987 | Petersen . |
| 4,706,660 | 11/1987 | Petersen . |
| 4,710,075 | 12/1987 | Davison ................................ 408/202 |
| 5,021,055 | 6/1991 | Burkinshaw et al. .................. 606/82 |
| 5,108,401 | 4/1992 | Insall et al. ............................ 606/79 |
| 5,129,907 | 7/1992 | Heldreth et al. ....................... 606/80 |
| 5,129,908 | 7/1992 | Petersen ................................. 606/88 |
| 5,147,365 | 9/1992 | Whitlock et al. ...................... 606/88 |
| 5,180,384 | 1/1993 | Mikhail ................................. 606/80 |
| 5,342,364 | 8/1994 | Mikhail ................................. 606/79 |

OTHER PUBLICATIONS

Smith & Nephew Richards Genesis™ Total Knee System Catalog (Sep. 1992).

*Primary Examiner*—Guy V. Tucker
*Attorney, Agent, or Firm*—Pravel, Hewitt, Kimball & Krieger

[57] ABSTRACT

An improved patella clamp apparatus includes a scissor-like instrument frame having a pair of handles at one end portion. A patella holder and drill collet have gripping surfaces for holding a patient's patella therebetween during preparation for implantation of a prosthesis. The collet has arcuate slots for accepting the vertical ridge of the patella. A reamer or cutting instrument cuts a circular recess into the posterior face of the patella. The collet is supported by the frame and positioned opposite the elevator. The collet accepts a depth stop for referencing the posterior aspect of the patella. The collet provides a bore that supports a reamer or drill for forming the circular recess in the patella posterior surface.

14 Claims, 5 Drawing Sheets

PATELLA CLAMP APPARATUS

BACKGROUND OF THE INVENTION:

1. Field of the Invention

The present invention relates to orthopedic surgical instruments, such as surgical guides, surgical cutting instruments, and the like that are used to remove a predetermined amount of the patient's patella so that the patella can receive a prosthesis as part of knee joint replacement surgery. Even more particularly, the present invention relates to an improved patella clamp apparatus that will allow the user to center the cut (eg. a reamer cut) on the patella vertical ridge by providing a reamer collet that can be offset with respect to a patella holding jaw that cradles the patella during cutting.

2. General Background

In total knee arthroplasty, the patella usually requires a new articular surface. This new surface can be obtained using an implant designed to conform to the geometry of the mating femoral implant. It is important that the patella position and tracking be reproduced with the implants. Thus, the instrument must be easy to use and yield reproducible results.

There are primarily two types of patella implants. One type requires a resurfacing of the patella. The other type requires that an inset or cavity be prepared for receiving the implant. With the resurfacing patella implant, the patella requires a flat plane for placement of the implant thereon. This plane is typically obtained by using a sawing or a reaming technique.

A second type of implant is the inset patella implant. The inset patella implant requires an inset surface in the patella to place the implant. This surface can only be obtained by a reaming type instrument.

There are a number of issued patents that are concerned with patella clamps in general. These prior art patella clamp instruments provide the user with either a reamer-type cutting apparatus or a saw-type cutting apparatus.

A recently issued patent, entitled "Method For Implanting A Patellar Prosthesis", is issued to W. E. Mikhail, U.S. Pat. No. 5,180,384. The Mikhail patent discloses a method for preparing a patella for receiving a patellar implant and for implanting a prosthesis therein. An elongated passageway is formed in the patella which is then reamed to form a cavity of a size and configuration to receive the patella prosthesis using a cannulated reamer telescoped over a guide rod positioned in the elongated passageway.

The Whitlock et al. U.S. Pat. No. 5,147,365 discloses a patella osteotomy guide comprising a plier-like appliance with curved jaws for grasping a patient's patella. A row of teeth faces inwardly from the jaws. The teeth are generally of pyramid shape, but a vertex of each tooth lies in a plane containing a bottom side of the respective jaw. Each of the jaws has an integral saw capture slot and the tips of the jaws are extended. A rotating, calibrated stylus measures the position of the patella with respect to the integral saw capture slots. The rotating stylus also functions as a pivot or fulcrum about which the jaws and handles of the osteotomy guide rotate. Handles for the osteotomy guide are offset from the plane of the jaws. The rotating stylus can be displaced up and down and then locked into a selected position using a draw bar and captured balls. A bowed retaining ring imparts a certain amount of pre-load to the stylus and draw bar assembly to hold the assembly in a selected position.

A patella cutting clamp is disclosed in U.S. Pat. No. 5,108,401 issued to Insall et al. The Insall device discloses a patella cutting clamp that comprises a pair of jaw members joined together in scissors-like relation for pivotal movement relative to each other about a pivot axis intermediate their ends. Each jaw member has a handle portion extending in one direction from the pivot axis and a jaw portion extending in the other direction. The jaw portions have edges facing each other that are shaped for engagement with opposite borders of a patella. Teeth along the patella-gripping edges grip and hold the patella firmly. Saw guide slots in the jaw portions lying in a common plane guide the saw when the saw cut is made. A patella elevator member is attached to the jaw members for movement along the pivot axis and has a platform portion adapted to engage the anterior aspect of the patella. A mechanism is provided for establishing and maintaining a predetermined position of the elevator member relative to the jaw members and thereby positioning the patella at a predetermined position relative to the saw guide slots. Another mechanism holds the jaw members in an adjusted position relative to each other with the jaw portions engaging and holding the patella.

U.S. Pat. No. 5,129,908 issued to Thomas Petersen and entitled "Method And Instruments For Resection Of The Patella" discloses a method of performing surgery to resect the patella for purpose of installing a patellar prosthesis, along with instruments used in such surgery. The instruments include a combined clamping device and reaming guide which when clamped about the patella provides a guide for reaming the surface thereof as well as a limit stop device designed to prevent reaming the patella too deeply. The instruments also include a reaming device designed to ream an annulus of material from the patella, leaving a central raised portion for fixation of a patellar prosthesis.

A patellar clamp and reamer with an adjustable stop is disclosed in the Heldreth U.S. Pat. No. 5,129,907. The '907 patent discloses a patellar clamp and reamer for performing either a total surfacing procedure or insetting procedure for preparing the patellar surface for a prosthetic implant, including an adjustable stop connected to the clamp and engaging a collar on the reamer shaft to space the reamer blade a calibrated distance from the clamp's reference jaw. The stop is calibrated and includes indicator thereon in terms of the thickness of patellar bone to remain after resection.

The Burkinshaw et al. U.S. Pat. No. 5,021,055 discloses a patellar clamp and surgical saw guide for preparing a patella to receive a prosthetic articulating surface on the patella's posterior side. A guide plate supports a saw block. The guide plate can be swiveled so that a sagittal saw can be presented to the patella from any desired angle. The saw block can be advanced or retracted axially so that more or less of the patella will be cut away by the sagittal saw. A scale enables the location of the proposed cut to be quickly and accurately determined. Storage apparatus in a handle of the clamp holds different specialized tools for use during surgery.

A patella clamp is disclosed in the Petersen U.S. Pat. No. 4,706,660 which includes a fixed jaw having a spike centrally disposed on a part spherical surface with this spike being axially aligned with a reciprocating plunger. The plunger is operated by a second handle pivotally disposed with respect to the first handle and spring biasing means between the handles biases them in a direction of separation of the plunger and spike.

Another Petersen U.S. Pat. 4,633,862 entitled "Patellar Resection Sawguide" discloses a method and instruments for the installation of a patellar button prosthesis. The first instrument consists of a saw guide including gauges integrally attached thereto which aid the surgeon in determining whether the patella has been grasped at the correct location with respect to the anterior and posterior sides thereof, which determine for the surgeon whether adequate bone stock will remain after resection of the patella, and which are chosen to correspond with the particular thickness of the patellar button which is to be installed. The second instrument consists of a drill guide including structure enabling its attachment to one of the jaws of the saw guide so that the saw guide may be retained in position about the patella after resection. A further instrument usable with the present invention consist of a drill bit including a collar which is provided to interact with holes formed in the drill guide to as to limit the depth of the holes which are drilled in the patella for the purpose of installation of the patellar button. Finally, a patella clamp is provided which includes a single moveable jaw limited in its movement solely to reciprocation, which clamp is utilized to install the patellar button onto the resected patella. The disclosed method involves the use of the above described instruments for the purpose of installation of a patellar button prosthesis.

The Shapiro U.S. Pat. No. 4,565,192 discloses a device for cutting a portion of a patella during knee surgery in which the articular surface of the patella along with a portion of the bone of the patella is cut away for implantation of a prosthesis. The device disclosed provides a fixed clamping member and an adjustable clamping member which clamp the patella and space from the patella a support surface for an oscillating saw used in the cutting of the patella. The precise plane of cut is provided by the use of a placement aid which is used according to the method of the present invention. The placement aid positions the support surface a precise depth below the articular surface of the patella during the clamping procedure, which clamping procedure also horizontally levels the support surface and the device so that all cuts through the patella are made in a perfectly horizontal place. Spacers are also provided which are mountable over the support surface and are used to allow for progressively deeper cuts to be made in the patella through parallel horizontal planes of cut by allowing interchanges of one spacer for another of less thickness. Each spacer has its own flat surface that allows support of the oscillating saw thereon for cutting through the patella during that particular cut as defined by the thickness of the spacer used.

SUMMARY OF THE INVENTION:

The present invention provides an improved patella clamp apparatus that allows a surgeon adjustability when gripping the patient's patella so that the rotary cut can be placed at the patella ridge even if the patella ridge is not the "center" of the patella.

The apparatus of the present invention includes an instrument frame having handles for manually supporting the frame. The patella can be held during a surgical preparation of the patella with a holder mounted on one arm of the frame and a guide that slidably engages the other arm of the frame.

The guide member has teeth for engaging the patella and recesses that conform generally to the shape of the patella ridge. A holding surface on one of the arms provides a concave surface for cradling the patella and a plurality of spikes for gripping the patella.

A drill guide is movably supportive upon the frame and positioned generally opposite the holding surface. The guide is movable along a line generally parallel to the plane of the holding surface and to multiple adjustment positions relative to the center of the holding surface.

The guide provides a cylindrically shaped bore that supports a rotary reamer cutting instrument that prepares the patella posterior surface to receive a prosthetic patella, generally circular.

Lateral movement of the guide upon the frame defines a position of cuts to be made into the patient's patella so that the cuts can be centered on the patient's patella ridge, not necessarily the center of the patella.

An adjustment is provided for defining the depth of cut. The adjustment includes a stop housing mounted on a drive shaft of the reamer. The stop housing has a lower surface that abuts the upper surface of the guide.

A gauge is provided for setting the depth of cut by setting a distance between the top of the guide and the bottom of the stop housing when the cutting instrument just touches the patella tissue to be cut. Also the gauge determines diameter. The gauge can include a number of thicknesses for defining different depths of cuts such as for example 10 mm, 12 mm, and 14 mm. The gauge also determines the diameter of the prosthesis to be used such as 23 mm, 26 mm, or 29 mm. For example, if the surgeon wants to use a 26 mm diameter prosthesis, the gauge automatically sets a 10 mm depth of cut.

The frame can include a pair of spaced apart arms having handles that allow the surgeon to hold both handles simultaneously.

A spring urges the arms apart and a threaded shaft with a nut mounted thereon defines the distance between the arms. Further, a tightening of the nut upon the threaded shaft forces the holder and guide together so that the teeth on the guide bite into the patella on one side and the spikes of the holder bite into the patella on the other side for a firm grip.

An adjustment of depth of cut is preferably provided by a stop assembly mounted on the drive shaft of the reamer. A plurality of spaced apart teeth with grooves therebetween are provided on the drive shaft of the reamer. The reamer stop housing can be attached to selected grooves by pushing a knob on a stop guide that is movable with respect to the stop housing. Thus, the surgeon simply pushes the knob to release the stop from the drive shaft, moves the stop housing vertically to a desired position, and then releases the stop guide so that it bites into the drive shaft, registering into one of the grooves.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figures 1, 2:
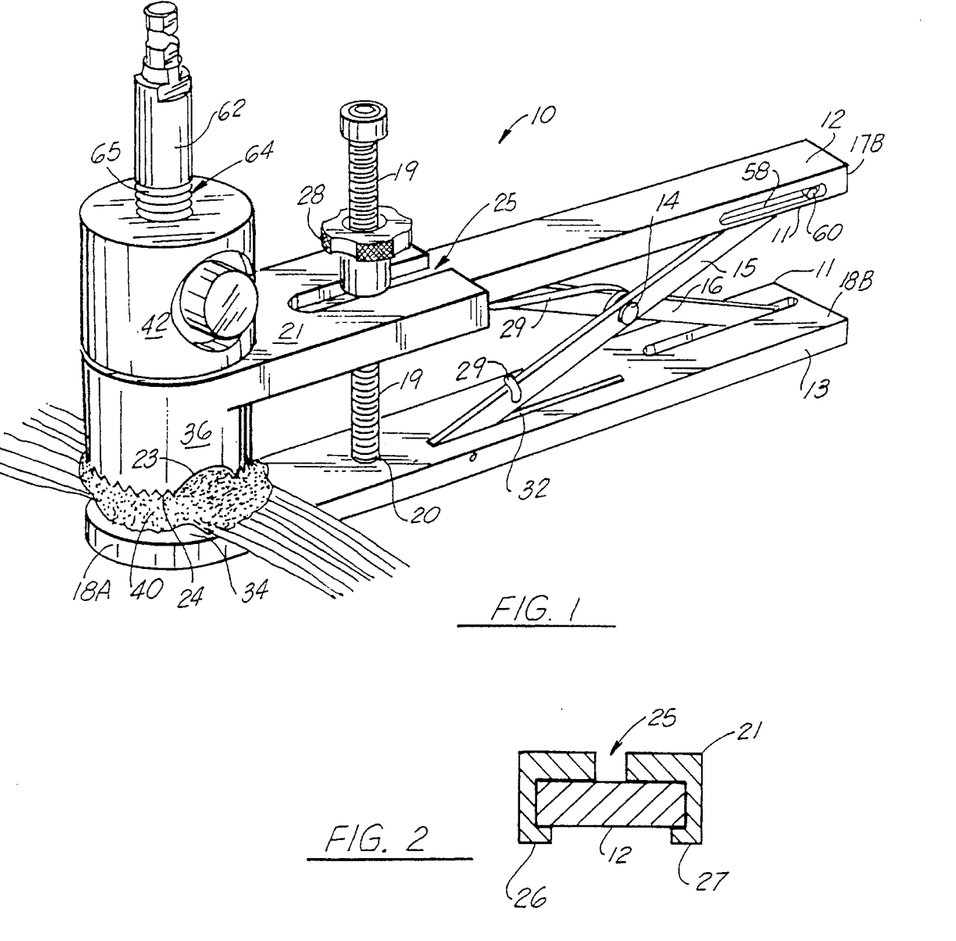
FIG. 1 is a perspective view of the preferred embodiment of the apparatus of the present invention.
FIG. 2 is a fragmentary sectional view of the preferred embodiment of the apparatus of the present invention illustrating the connection between the instrument frame and guide assembly.

FIG. 1 shows generally the preferred embodiment of the apparatus of the present invention designated generally by the numeral 10. Patella clamp apparatus 10 includes an instrument frame 11 that comprises a pair of spaced apart and generally parallel arms 12, 13. The arms are joined by a pair of diagonal struts 15, 16 that intersect at pivot 14. Each of the arms 12, 13 includes a distal end portion 17A, 18A respectively that carry a guide member 21 and a patella holder 34 as will be described more fully hereinafter.

A threaded rod 19 is attached to the lower arm 13 at weld 20. Guide member 21 slides with respect to the central longitudinal axis of upper arm 12 as indicated by the arrows 21A in FIG. 4. Guide member 21 provides a cylindrically shaped bore 22 that holds a rotary reamer 60 during surgical preparation of the patient's patella 40. The guide member 21 provides a pair of spaced apart curved tooth sections 24 with a pair of arcuate recesses 23 therebetween. The recesses 23 conform to the patella ridge 41 during surgical preparation (reaming) of the patella as the reamer cutting blade element 61 centers its cuts on the patella ridge 41 (see FIG. 4).

Figure 3:
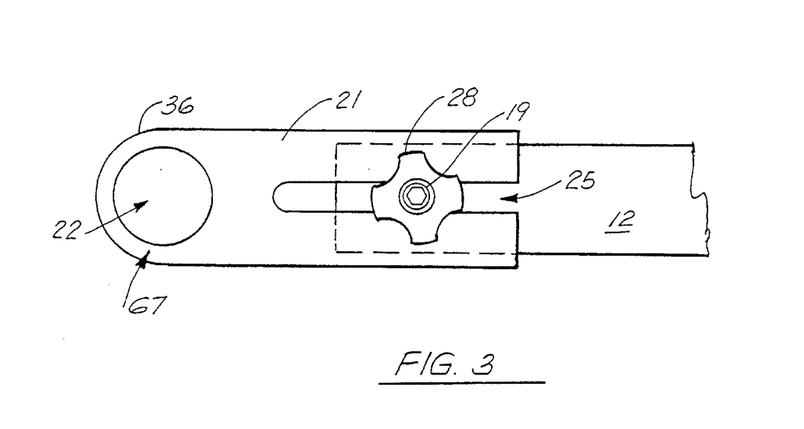
FIG. 3 is a top fragmentary view of the preferred embodiment of the apparatus of the present invention.
Figures 4, 4A, 5:
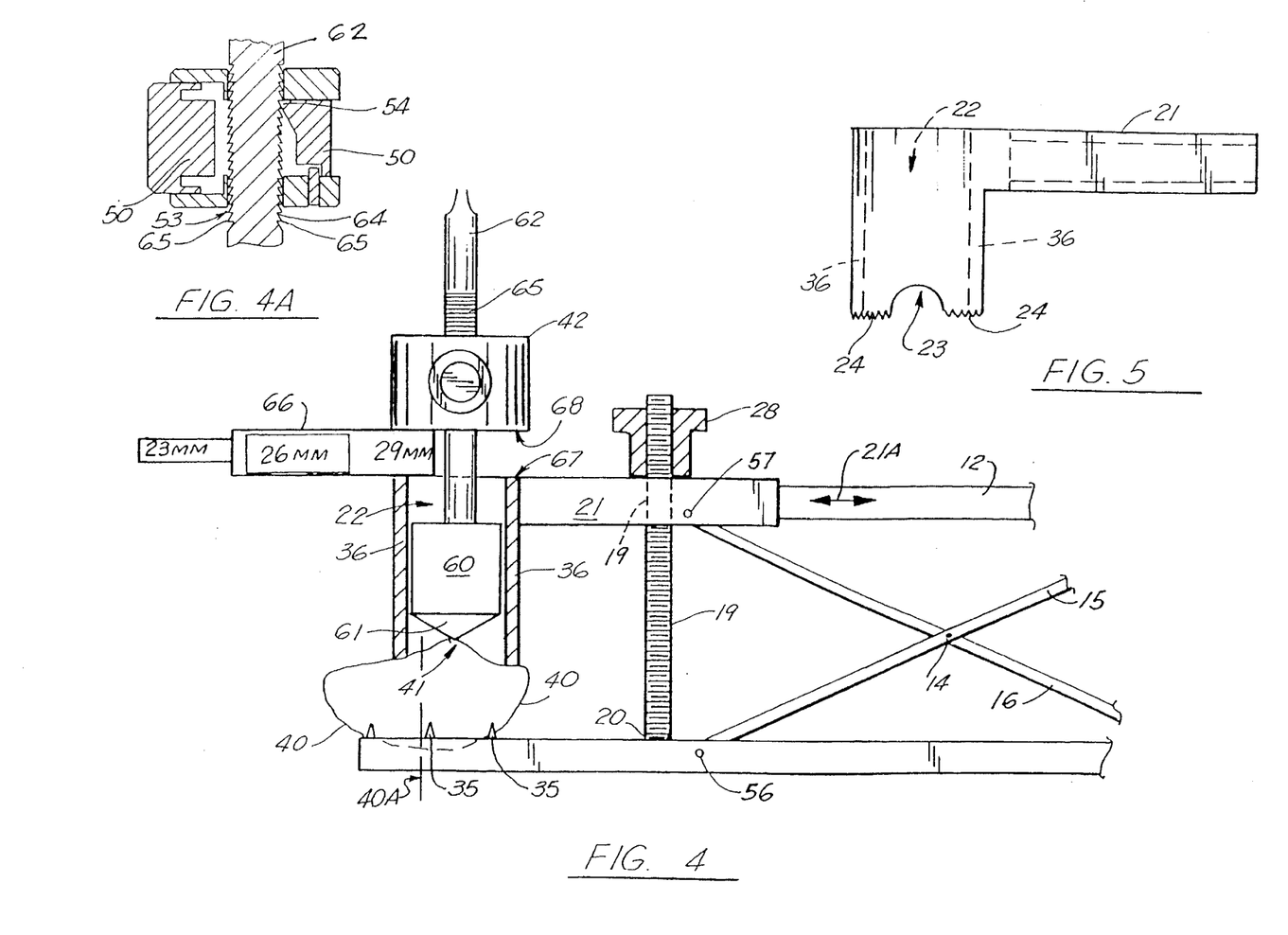
FIG. 4 is an elevational fragmentary view of the preferred embodiment of the apparatus of the present invention.
FIG. 4A is a fragmentary sectional elevational view illustrating the reamer drive shaft and stop member in an engaged position.
FIG. 5 is a partial elevational view of the preferred embodiment of the apparatus of the present invention illustrating the guide portion thereof.
Figure 6:
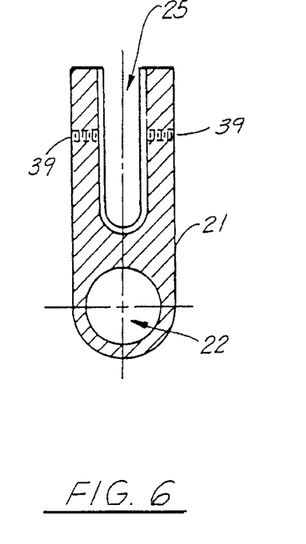
FIG. 6 is a top sectional view of the guide portion of the preferred embodiment of the apparatus of the present invention.
Figure 7:
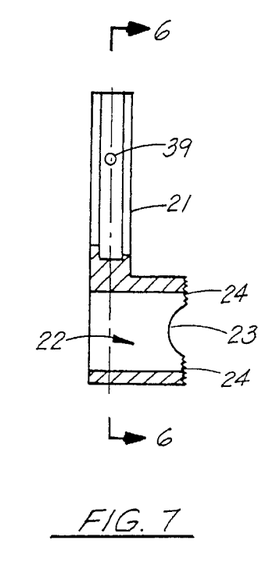
FIG. 7 is a side, partial sectional view of the guide portion of the preferred embodiment of the apparatus of the present invention.
Figure 8:
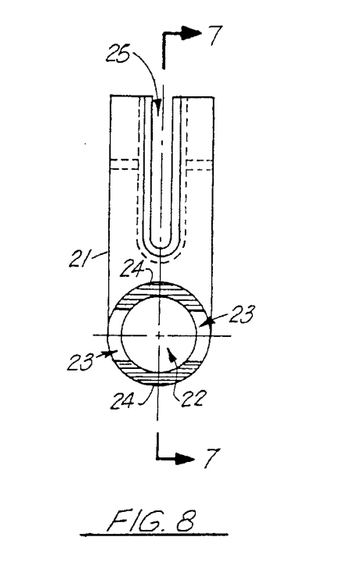
FIG. 8 is a bottom view of the guide portion of the preferred embodiment of the apparatus of the present invention.

Guide member 21 includes a longitudinally extending slot 25 that fits the threaded member 19 as shown in FIGS. 1, 3, and 4. The guide member 21 also includes a pair of longitudinally extending flanges 26, 27 that hold the guide member 21 to the upper arm 12 as shown in FIG. 2. A nut 28 can be used to adjust the distance between upper and lower arms 12, 13 by rotating the wing nut 28 upon threaded member 19. Wing nut 28 threadably engages member 19 shown in FIG. 4. Spring 29 urges the upper and lower arms 12, 13 apart. However, the wing nut 28 acts a stop, limiting the distance that the arms 12, 13 can move away from each other.

The scissor-like diagonal struts 15, 16 maintain the arms 12, 13 in a generally parallel relationship. The diagonal struts 15, 16 are each pinned at pinned connection 56, 57 respectively to the arms 13, 12 respectively.

Figure 9:
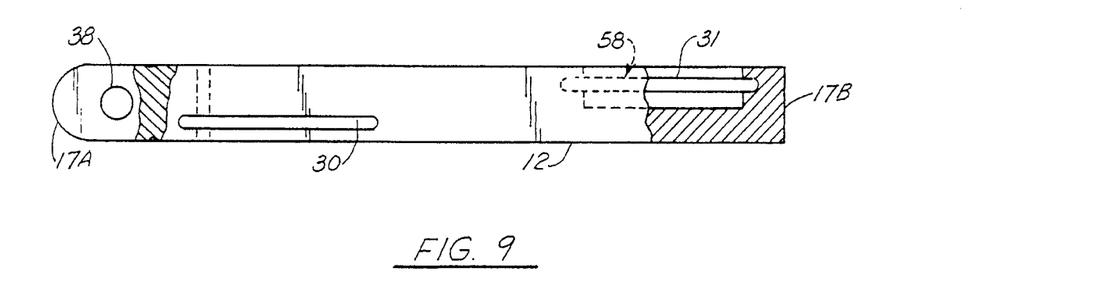
FIG. 9 is a partial view of the preferred embodiment of the apparatus of the present invention illustrating a portion of the instrument frame.
Figure 10:
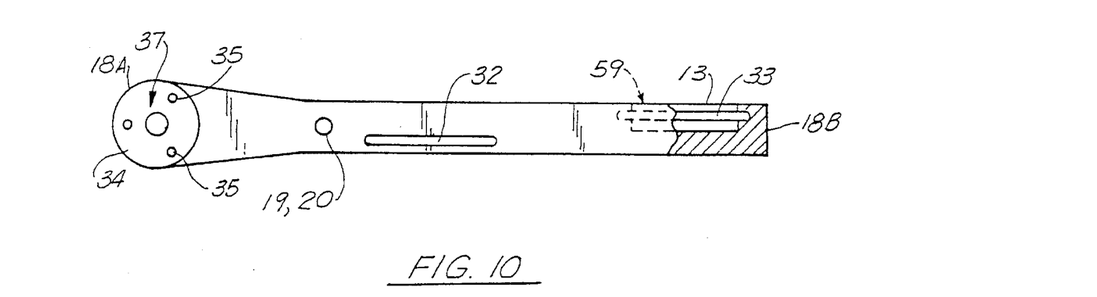
FIG. 10 is a partial view of the preferred embodiment of the apparatus of the present invention illustrating a portion of the instrument frame.

Each end portion of each strut 15, 16 travels in a slot that extends longitudinally along the arms 12, 13. In FIGS. 1, 9, and 10, struts 15 can be seen fitted to the longitudinally extending slot 32 of arm 13 and slot 31 of upper arm 12. Similarly, diagonal strut 16 fits slot 33 of the lower arm 13 and the slots 30 of upper arm 12. The diagonal member 15 thus extends between the slots 31 (of upper arm 12) and 32 (of lower arm 13). The diagonal member 16 extends between slot 30 of arm 12 and slot 33 of arm 13. The arms 15, 16 slide in the slots 31, 33 respectively. Each of the respective diagonal members 15, 16 is pinned at pinned connections 56, 57 respectively to arms 12, 13. The arm proximal ends 17B, 18B each provide laterally extending pins 60 that engage the slots 58, 59. Slots 58, 59 communicate with the slots 31, 33.

A patient's patella 40 typically has a projecting portion known as the patella ridge 41. The patella ridge 41 is not always located at the center 40A of the patient's patella. As shown in FIG. 4, the patella ridge 41 can be offset with respect to the actual center 40A of the patient's patella 40. The apparatus 10 of the present invention accommodates for such an offset by allowing the guide 21 to adjust longitudinally along upper arm 12. Thus, a rotary reamer 60 can be desirably centered on the patient's patella ridge 41 as shown in FIG. 4 before the surgeon activates the reamer to cut an opening for receiving a patella implant.

Lower arm 13 provides a holder 34 for holding the patient's patella 40. Holder 34 provides a concavity 37 lined with a plurality of spikes 35 as shown in FIG. 10. The spikes 35 extend upwardly for engaging the patella 40 which is placed under the cylindrical wall 36 of guide 21, and gripped by teeth 24. Reamer 60 is then placed within the bore 22 of guide 21. An opening 38 in upper arm 12 accepts threaded member 19. One or more transverse, internally threaded openings 39 in guide member 21 can be used for holding externally threaded set screws. Set screws can be optionally used for immobilizing guide 21 with arm 12 once a particular location of guide 21 is selected. Wing nut 28 also immobilizes guide 21 once it is tightened to force teeth 24 against patella 40 and its holder 34.

Figure 11:
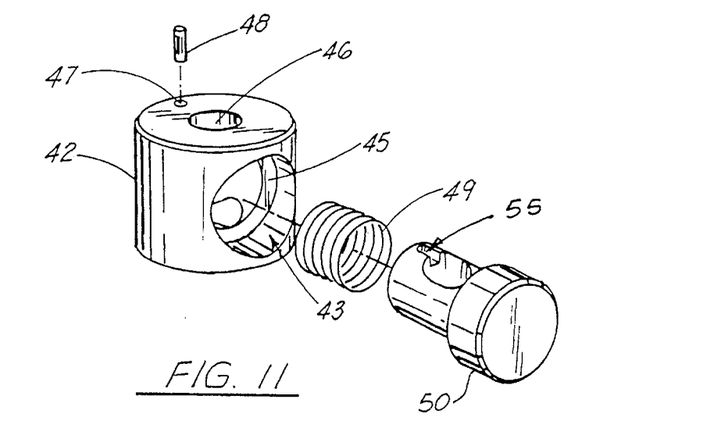
FIG. 11 is a partial fragmentary perspective view of the preferred embodiment of the apparatus of the present invention illustrating the reamer stop portion thereof.

In FIGS. 1, 4, 4A, and 11–15, reamer stop housing 42 is shown. In FIG. 11, housing 42 and stop guide 50 are viewed from below for better illustrating pin 48 and slot 55. The reamer stop housing 42 mounts upon reamer 60 at drive shaft 62 and defines the depth of cut to be made by a blade element 61 at the lower end of reamer 60. Reamer stop housing 42 includes a larger diameter cylindrically-shaped opening 43 and a smaller diameter cylindrically-shaped opening 44. The openings 43, 44 share a common axis 58.

Figure 12:
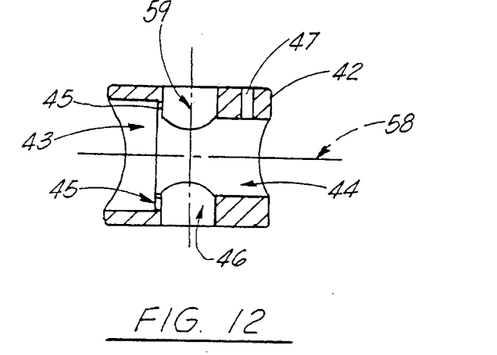
FIG. 12 is a fragmentary sectional view of the preferred embodiment of the apparatus of the present invention illustrating a portion of the reamer stop.
Figure 13:
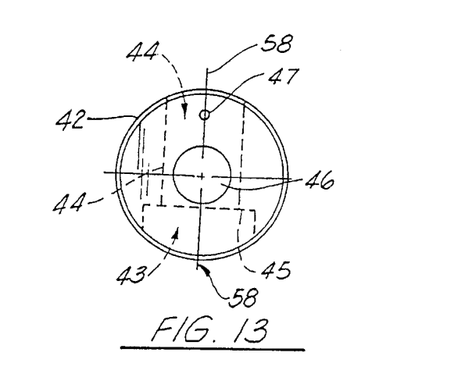
FIG. 13 is a top view of the reamer stop housing portion of the preferred embodiment of the apparatus of the present invention illustrating a portion of the reamer stop.
Figure 14:
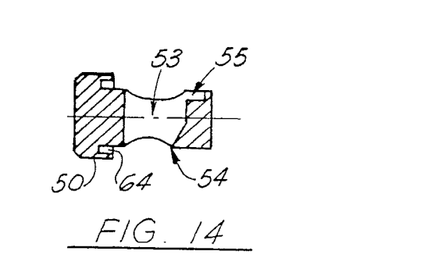
FIG. 14 is a fragmentary sectional view of the preferred embodiment of the apparatus of the present invention illustrating a portion of the reamer stop.
Figure 15:
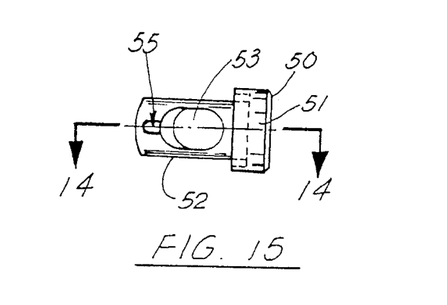
FIG. 15 is a fragmentary top view of the preferred embodiment of the apparatus of the present invention illustrating a portion of the reamer stop.

Annular shoulder 45 is positioned at the intersection of opening 43, 44. Vertical bore 46 intersects axis 58 at approximately right angles as shown in FIGS. 12 and 13. Reamer drive shaft 62 fits vertical bore 46, tracking its central longitudinal axis 59.

Pin opening 47 accepts stop pin 48. Stop pin 48 extends into small diameter cylindrical opening 44 and into horizontal slot 55 of stop guide 50. In this fashion, the user can push on the stop guide 50 in order to release the drive shaft 62 of rotary reamer 60 allowing for vertical, depth of cut adjustment. Coil spring 49 surrounds the stop 54 of stop guide 50, registering in annular slot 63. Spring 49 also bears against annular shoulder 45 urging the stop 54 into engagement with the outer surface of shaft 62 thereby setting the position of housing 42 relative to drive shaft 62 (see FIG. 4A).

In order to select a particular depth of cut, the user pushes knob 51 of stop guide 50 overcoming spring pressure supplied by coil spring 49. This disengages the stop 54 from the outside surface of drive shaft 62. This also removes the stop 54 from engaging the annular spaces 64 between the adjacent teeth 65 of drive shaft 62. A gauge 66 can be used to measure the depth of cut by placing the gauge between the upper surface 67 of guide member 21 and the lower surface of 68 of stop housing 42. Releasing the stop guide 50 at the desired position then affixes stop 50 to a space 64 between adjacent teeth 65.

Figure 17:
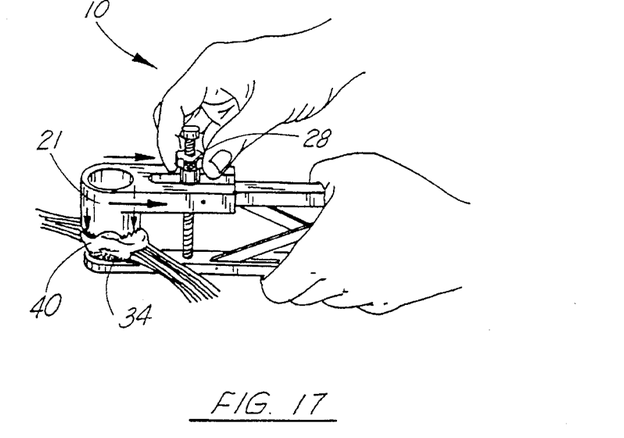
FIGS. 17–19 are perspective schematic views that illustrate the patella clamp apparatus of the present invention in use when preparing a patient's patella to receive a surgical implant.
Figure 18:
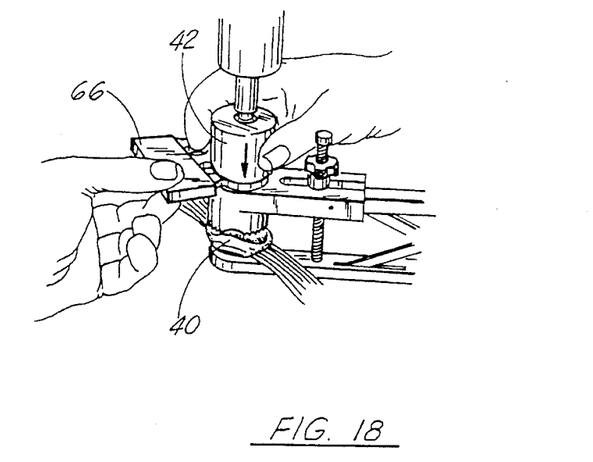
Figure 19:
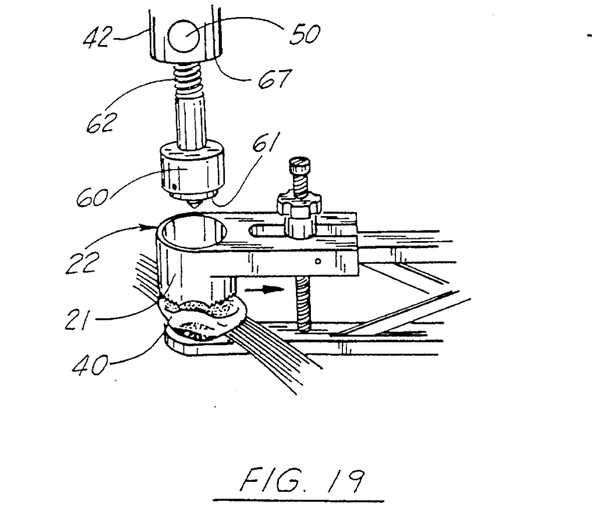

FIGS. 17–19 illustrate the surgical method of the present invention using the apparatus 10 of the present invention. In FIG. 17, patella clamp apparatus 17 has been placed in an inoperative position with the patient's patella 40 in between holder 34 and the teeth of guides 21. The surgeon loosens the wingnut 28 as shown and adjusts the guide member 21 until the recess 23 of guide 21 is placed at the patient's patella ridge 41. The surgeon then tightens the wingnut 28 until the teeth 24 of guide 21 firmly grips the patella on one side and the spikes 35 of holder 34 on the opposing side of the patella 40.

The surgeon then uses the gauge 66 to select a particular diameter prosthesis and to also set the appropriate depth of cut. The surgeon uses the gauge (see FIGS. 4 and 16) to select a diameter and depth of cut that the surgeon believes is appropriate for the particular patella 40 being prepared. The gauge 66 provides a plurality of gauge arms 69, 71, 73. These arms can extend from a central hub 75 or can be mounted parallel on a rectangular member (see FIG. 18). Each of the arms provides a recess 70, 72, 74 respectively that fits about the drive shaft 62 of rotary reamer 60. A particular gauge arm 69, 71, 73 is of a particular thickness. For example, thicknesses of 10 mm, 12 mm, and 14 mm are exemplary. In FIG. 4, a 14 mm thickness arm has been placed in between the upper surface 67 of guide member 21 and the lower surface 68 of stop housing 42. This 14 mm thickness corresponds to a prosthesis diameter of 29 mm.

Figure 16:
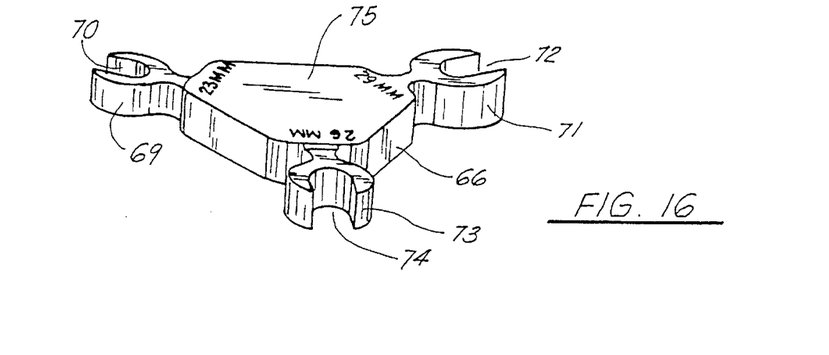
FIG. 16 is a perspective view illustrating the gauge portion of the preferred embodiment of the apparatus of the present invention.

In the preferred embodiment, the gauge 66 is configured as shown in FIG. 16. However, the gauge can be an elongated rectangular structure as shown in FIG. 18, having three gauge arms extending at right angles thereto. In FIG. 16, the gauge arm 69 has a thickness of 10 mm and a recess 74 registering with the drive shaft 62. The gauge arm 61 has a thickness of 14 mm and a recess 72 for registering with the drive shaft 62. The gauge arm 73 has a thickness of 12 mm and a recess 74 for registering with the drive shaft 62.

In FIG. 19, the stop guide 50 has been engaged so that the stop 54 engages one of the annular teeth 65 or annular groove of drive shaft 62. This affixes the position of reamer stop housing 42 and more particularly its under side 67. The surgeon then places the reamer 60 in the bore 22 and allows the reamer cutting blade elements 61 to engage the patient's patella 40. A rotary driver (not shown) is used to power and rotate the reamer 60. The cutting elements 61 surgically cut the patella 40 to perform a circular recess that will accept a patella implant. The depth of cut is governed by the registration of under surface 67 of stop housing 42 against the upper surface 67 of guide member 21.

The following table lists the parts numbers and parts descriptions as used herein and in the drawings attached hereto.

| PARTS LIST | |
|---|---|
| Part Number | Description |
| 10 | apparatus |
| 11 | instrument frame |
| 12 | upper arm |
| 13 | lower arm |
| 14 | pivot |
| 15 | diagonal strut |
| 16 | diagonal strut |
| 17A | distal end |
| 17B | proximal end |
| 18A | distal end |
| 18B | proximal end |
| 19 | threaded rod |
| 20 | weld |
| 21 | guide member |
| 21A | arrows |
| 22 | bore |
| 23 | arcuate recess |
| 24 | toothed sections |
| 25 | slot |
| 26 | flange |
| 27 | flange |
| 28 | wingnut |
| 29 | spring |
| 30 | slot |
| 31 | slot |
| 32 | slot |
| 33 | slot |
| 34 | holder |
| 35 | spike |
| 36 | cylindrical wall |
| 37 | concavity |
| 38 | opening |
| 39 | opening |
| 40 | patella |
| 40A | center of patella |
| 41 | patella ridge |
| 42 | reamer stop housing |
| 43 | larger diameter opening |
| 44 | smaller diameter opening |
| 45 | annular shoulder |
| 46 | vertical bore |
| 47 | pin opening |
| 48 | stop pin |
| 49 | coil spring |
| 50 | stop guide |
| 51 | knob |
| 52 | cylindrical section |
| 53 | vertical opening |
| 54 | stop |
| 55 | horizontal slot |
| 56 | pinned connection |
| 57 | pinned connection |
| 58 | axis |
| 59 | axis |
| 60 | rotary reamer |
| 61 | blade element |
| 62 | shaft |
| 63 | |
| 64 | annular groove |
| 65 | annular tooth |
| 66 | gauge |
| 67 | upper surface |
| 68 | lower surface |

-continued

PARTS LIST

| Part Number | Description |
| --- | --- |
| 69 | gauge arm |
| 70 | recess |
| 71 | gauge arm |
| 72 | recess |
| 73 | gauge arm |
| 74 | recess |
| 75 | hub |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A patella clamp and rotary cutting apparatus comprising:
   a) an instrument frame that includes handle means for manually supporting the frame the frame having proximal and distal end portions;
   b) a holder for manipulating the patella during a surgical preparation of the patella by engaging a side of the patella opposite the side to be surgically cut, said holder having a patella holding surface that defines a plane for holding the patella in a desired position, said holding surface having a center;
   c) a drill guide movably supported upon the frame and positioned generally opposite the patella holding surface, the guide being movable along a line generally parallel to the plane of the holding surface into multiple positions relative to the center of the patella holding surface;
   d) the drill guide providing a bore;
   e) a rotary cutting instrument that fits the drill guide bore for surgically preparing the patella posterior surface to receive a prosthetic patella;
   f) wherein movement of the drill guide upon the frame enables a surgeon to offset the central axis of the rotary cutting instrument with the center of the holder to define the position of cuts to be made both proximally and distally of the rotary cutting instrument into the patient's patella in relation to the center of the patella;
   g) the rotary cutting instrument registering with the guide at a preselected depth of cut position relative to the patella so that the guide prevents the cutting instrument from cutting too deeply into the patella; and
   h) the rotary cutting tool having an adjustment thereon for defining the depth of cut made by the cutting instrument into the patella, enabling a surgeon to adjust the depth of cut on the rotary cutting tool while the frame is holding the patella.

2. The apparatus of claim 1 wherein the handle means comprises a pair of opposed handles.

3. The apparatus of claim 1 wherein the frame comprises a pair of frame halves.

4. The apparatus of claim 1 wherein the holding surface is generally rounded.

5. The apparatus of claim 1 wherein the guide is generally cylindrically shaped.

6. The apparatus of claim 1 wherein the frame comprises a pair of frame halves that are parallel to one another.

7. The apparatus of claim 1 wherein the rotary cutting instrument includes a drive shaft.

8. The apparatus of claim 7 wherein the adjustment includes annular adjustment positions spaced along the drive shaft.

9. The apparatus of claim 1 further comprising feeler gauge means for measuring the depth of cut.

10. The apparatus of claim 1 wherein the adjustment comprises a stop assembly mounted on the rotary cutting instrument for stopping movement of the cutting instrument relative to the drill guide.

11. The apparatus of claim 10 wherein the adjustment includes a stop assembly mounted on the cutting instrument and positioned to abut the drill guide for limiting the depth of cut.

12. A patella clamp and rotary cutting apparatus comprising
   a) an instrument frame that includes handle means for manually supporting the frame the frame, having proximal and distal end portions and a patella holder with a center;
   b) a drill guide collet, supported at one end of the instrument frame, the collet providing a bore that supports a rotary cutting instrument for preparing a patient's patella posterior surface for receiving a prosthetic patella;
   c) a rotary cutting instrument that fits the grill guide collet;
   d) the rotary cutting instrument having an adjustment thereon for enabling a surgeon to set a desired depth of cut into the patient's patella;
   e) the rotary cutting instrument having a center of rotation; and
   f) the frame and drill guide collet being slidably connected for adjusting the position of center cut both proximally and distally relative to the center of the patella holder.

13. The apparatus of claim 12 wherein the frame comprises a pair of frame arms that are generally parallel.

14. A patella clamp and rotary cutting apparatus comprising:
   a) an instrument frame that includes handles for manually supporting the frame, the handles including a pair of frame arms, the frame having proximal and distal end portions and a patella holder with a center;
   b) a collet, supported by the frame at one of the arms and providing a bore;
   c) a rotary cutting instrument having a center of rotation that fits the collet for preparing the patella posterior surface to receive a prosthetic patella;
   d) an adjustable member for moving the collet along one of the frame arms into multiple positions relative to the frame so that said center of rotation is adjustable both proximally and distally relative to the center of the patella holder;
   e) the rotary cutting instrument having an adjustable stop thereon for defining the depth of cut of a rotary cutting instrument into the patella, enabling a surgeon to adjust the depth of cut on the rotary cutting tool while the frame is holding the patella.

* * * * *